US007651695B2

(12) United States Patent
Roorda et al.

(10) Patent No.: US 7,651,695 B2
(45) Date of Patent: *Jan. 26, 2010

(54) MEDICATED STENTS FOR THE TREATMENT OF VASCULAR DISEASE

(75) Inventors: Wouter E. Roorda, Palo Alto, CA (US); Vinayak D. Bhat, Sunnyvale, CA (US); Steven L. Mouw, Mountain View, CA (US); Syed F. A. Hossainy, Fremont, CA (US); Steven Z. Wu, Santa Clara, CA (US); Deborra Sanders Millare, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 898 days.

This patent is subject to a terminal disclaimer.

(21) Appl. No.: 09/860,384

(22) Filed: May 18, 2001

(65) Prior Publication Data

US 2002/0188277 A1  Dec. 12, 2002

(51) Int. Cl.
 *A61F 2/00* (2006.01)
 *A61F 2/06* (2006.01)
(52) U.S. Cl. .................. 424/423; 623/1.42
(58) Field of Classification Search ............. 424/423; 623/1.42–1.48
 See application file for complete search history.

(56) References Cited

U.S. PATENT DOCUMENTS

| 2,072,303 | A | 3/1937 | Herrmann et al. ........... 606/230 |
|---|---|---|---|
| 4,977,901 | A | 12/1990 | Ofstead ..................... 128/772 |
| 5,328,471 | A | 7/1994 | Slepian .................... 604/101 |
| 5,464,650 | A | 11/1995 | Berg et al. .................. 427/2.3 |
| 5,578,073 | A | 11/1996 | Haimovich et al. ............ 623/1 |
| 5,605,696 | A | 2/1997 | Eury et al. .................. 424/423 |
| 5,609,629 | A * | 3/1997 | Fearnot et al. ............ 623/1.42 |
| 5,628,730 | A | 5/1997 | Shapland et al. ............. 604/21 |
| 5,667,767 | A | 9/1997 | Greff et al. ............... 424/9.411 |
| 5,670,558 | A | 9/1997 | Onishi et al. ................ 523/112 |
| 5,700,286 | A | 12/1997 | Tartaglia et al. ............... 623/1 |
| 5,716,981 | A | 2/1998 | Hunter et al. ............... 514/449 |
| 5,733,925 | A | 3/1998 | Kunz et al. ................. 514/449 |
| 5,800,392 | A | 9/1998 | Racchini .................... 604/96 |
| 5,811,447 | A | 9/1998 | Kunz et al. ................. 514/411 |
| 5,824,049 | A | 10/1998 | Ragheb et al. ................ 623/1 |

(Continued)

FOREIGN PATENT DOCUMENTS

EP  0 665 023 A1  7/1994

(Continued)

OTHER PUBLICATIONS

Peter Barath, et al.; *Low Dose of Antitumor Agents Prevents Smooth Muscle Cell Proliferation After Endothelial Injury*; JACC vol. 13, No. 2; Feb. 1989:252A (Abstract).

(Continued)

*Primary Examiner*—David H Willse
*Assistant Examiner*—Javier G Blanco
(74) *Attorney, Agent, or Firm*—Squire, Sanders & Dempsey LLP

(57) ABSTRACT

The invention provides bioactive compositions and methods of delivery for ameliorating a vascular diseased state, particularly for the management of stenosis or restenosis following a vascular trauma or disease.

8 Claims, 4 Drawing Sheets

U.S. PATENT DOCUMENTS

| | | | | |
|---|---|---|---|---|
| 5,830,178 | A | 11/1998 | Jones et al. | 604/49 |
| 5,837,313 | A | 11/1998 | Ding et al. | 427/2.21 |
| 5,851,508 | A | 12/1998 | Greff et al. | 424/9.411 |
| 5,854,205 | A | 12/1998 | O'Reilly et al. | 514/2 |
| 5,865,814 | A | 2/1999 | Tuch | 604/265 |
| 5,873,904 | A | 2/1999 | Ragheb et al. | 623/1 |
| 5,971,954 | A | 10/1999 | Conway et al. | 604/96 |
| 5,980,928 | A | 11/1999 | Terry | 424/427 |
| 5,980,972 | A | 11/1999 | Ding | 427/2.24 |
| 6,010,530 | A | 1/2000 | Goicoechea | 623/1 |
| 6,015,541 | A | 1/2000 | Greff et al. | 424/1.25 |
| 6,096,070 | A | 8/2000 | Ragheb et al. | 623/1 |
| 6,153,252 | A | 11/2000 | Hossainy et al. | 427/2.3 |
| 6,165,212 | A | 12/2000 | Dereume et al. | 623/1.13 |
| 6,168,619 | B1 | 1/2001 | Dinh et al. | 623/1.13 |
| 6,197,051 | B1 | 3/2001 | Zhong | 623/1.46 |
| 6,210,436 | B1 | 4/2001 | Weadock | 623/1.39 |
| 6,251,136 | B1* | 6/2001 | Guruwaiya et al. | 623/1.46 |
| 6,281,225 | B1 | 8/2001 | Hearst et al. | 514/297 |
| 6,287,628 | B1* | 9/2001 | Hossainy et al. | 427/2.3 |
| 6,346,517 | B1* | 2/2002 | Wong et al. | 514/56 |
| 6,376,242 | B1* | 4/2002 | Hanson | 435/334 |
| 2001/0007083 | A1* | 7/2001 | Roorda | 623/1.15 |
| 2001/0027340 | A1 | 10/2001 | Wright et al. | 623/1.15 |
| 2002/0082685 | A1* | 6/2002 | Sirhan et al. | 623/1.42 |
| 2003/0129215 | A1* | 7/2003 | Mollison et al. | 424/426 |

FOREIGN PATENT DOCUMENTS

| | | |
|---|---|---|
| EP | 0 970 711 A2 | 6/1999 |
| EP | 1023879 | 8/2000 |
| WO | WO 91/12846 | 9/1991 |
| WO | 95/03036 | 2/1995 |
| WO | WO 97/45105 | 12/1997 |
| WO | 98/34669 | 8/1998 |
| WO | WO 00/12147 | 8/1999 |
| WO | 00/00238 | 1/2000 |
| WO | WO 00/02599 | 1/2000 |
| WO | WO 00/64506 | 4/2000 |
| WO | WO 01/01890 A1 | 6/2000 |
| WO | 00/62830 | 10/2000 |
| WO | WO 01/45763 | 6/2001 |
| WO | 01/47572 | 7/2001 |
| WO | 01/74414 | 10/2001 |

OTHER PUBLICATIONS

Taku Shigeno; *Prevention of Cerebrovascular Spasm by Bosentan, Novel Endothelin Receptor*; Kekkan to Naihi 6(4)(1996), pp. 416-421.

Yuji Matsumaru, et al.; *Embolic Materials For Endovascular Treatment of Cerebral Lesions*; J. Biomater. Sci. Polymer Edn, vol. 8, No. 7 (1997), pp. 555-569.

Norio Miyazawa, et al.; *Effects of Pemirolast and Tranilast on Intimal Thickening After Arterial Injury in the Rat*; J. Cardiovasc. Pharmacol. (1997), pp. 157-162.

Shozo Miyazaki, et al.; *Antitumor Effect of Implanted Ethylene-Vinyl Alcohol Copolymer Matrices Containing Anticancer Agents on Ehrlich Ascites Carcinoma and P388 Leukemia in Mice*; Chem. Pharm. Bull. (1985); pp. 2490-2498.

Hidefumi Ohsawa, et al.; *Preventive Effects of an Antiallergic Drug, Pemirolast Potassium, on Restenosis After Percutaneous Transluminal Coronary Angioplasty*; American Heart Journal (Dec. 1998); pp. 1081-1087.

Brehm et al.; *Prevention of human smooth muscle cell proliferation without induction of apoptosis by the topoisomerase I inhibitor topotecan*, Biochemical Pharmacology 61 (2001) 119-127.

Brem; *Angiogenesis and Cancer Control: From Concept to Therapeutic Trial*, Cancer Control Journal, vol. 6 No. 5.

Burstein, *Angiogenesis and Cancer: From the Bench to the Bedside*, American Society of Clinical Oncology 35th Annual Meeting.

Crea, *Screening for the restenosis subgroup: the role of humorl factors*, Istituto di Cardiologia, Università Cattolica, Roma.

de Scheerder et al., *Local methylprednisolone inhibition of foreign body response to coated intracoronary stents*, Coronary Artery Disease, Feb. 1996, vol. 7 No. 2, pp. 161-166.

Farb et al., *Pathology of Acute and Chronic Coronary Stenting in Humans*, Circulation, 1999; 99:44-52.

Gimbrone, Jr. et al., *Hemodynamics, Endothelial Gene Expression, and Atherogenesis*, Annals New York Academy of Sciences, pp. 1-11.

Jobin et al., *Curcumin Blocks Cytokine-Mediated NF-κB Activation and Proinflammatory Gene Expression by Inhibiting Inhibitory Factor I-κB Kinase Activity*, The Journal of Immunology, 1999, 163:3474-3483.

Jones et al., *Inhibition of angiogenesis by nonsteroidal anti-inflammatory drugs: Insight into mechanisms and implications for cancer growth and ulcer healing*, Nature Medicine, Dec. 1999, vol. 5, No. 12, pp. 1418-1423.

Khuri, *The Race Is On: New Drugs in Clinical Trials for Solid Tumors*, 10th European Cancer Conference (ECCO 10).

Komatsu et al., *Neointimal Tissue Response at Sites of Coronary Stenting in Humans*, Circulation, 1998; 98:224-233.

Lush et al., *Review of Three New Agents That Target Angiogenesis, Matrix Metalloproteinases, and Cyclin-Dependent Kinases*, Cancer Control Journal, vol. 6 No. 5.

Moreno et al., *Macrophage Infiltration Predicts Restenosis After Coronary Intervention in Patients With Unstable Angina*, Circulation, 1996; 94:3098-3102.

Nirmala et al., *Curcumin treatment modulates collagen metabolism in isoproterenol induced myocardial necrosis in rats*, Molecular and Cellular Biochemistry, 1999; 197:31-37.

O'Reilly et al., *Endostatin: An Endogenous Inhibitor of Angiogenesis and Tumor Growth*, Cell, Jan. 24, 1997, vol. 88, pp. 227-285.

Pietersma et al., *Late Lumen Loss After Coronary Angioplasty Is Associated With the Activation Status of Circulating Phagocytes Before Treatment*, Circulation, 1995; 91:1320-1325.

Shah et al., *Inhibitory Effect of Curcumin, a Food Spice from Turmeric, on Platelet-Activating Factor- and Arachidonic Acid-Mediated Platelet Aggregation through Inhibition of Thromboxane Formation and $Ca^{2+}$ Signaling*, Biochem. Pharmacol. 1999, 58;7: 1167-1172.

Shiff et al., *Aspirin for cancer*, Nature Medicine, Dec. 1999, vol. 5 No. 12, pp. 1348-1349.

*Current Focus*, EntreMed, http://www.entremed.com/prodtech/focus.html, printed Aug. 19, 1999, pp. 1-2.

*Antiangiogenesis*, EntreMed, http://www.entremed.com/prodtech/aa.html, printed Aug. 19, 1999, pp. 1-4.

*Endostatin reduced plaque development in mice*, Cardiology Today, http://www.slackinc.com/general/cardio/199908/mouse.asp, printed Aug. 18, 1999, pp. 1-3.

* cited by examiner

MEDICATED STENTS FOR THE TREATMENT OF VASCULAR DISEASE

BACKGROUND OF THE INVENTION

1. Field of the Invention

The invention relates to stents and bioactive compositions for ameliorating a vascular diseased state, particularly for the treatment of stenosis or restenosis following a vascular trauma or disease.

2. Description of the Background

Percutaneous transluminal intervention (PTI) is widely used as the primary treatment modality in many patients with coronary artery disease. PTI can relieve myocardial ischemia in patients with coronary artery disease by reducing lumen obstruction and improving coronary flow. Recurrent stenosis or restenosis, characterized by the reocclusion of the coronary arteries following PTI, remains a significant problem, however. Occurrence of immediate occlusion or development of restenosis within 6 months after the procedure, results in significant morbidity and mortality or frequently necessitates further interventions such as repeat angioplasty or coronary bypass surgery.

The processes responsible for restenosis after PTI are caused by complex interplay among several different biological agents and pathways. It has been theorized that the etiology of the disease process includes: (1) a shift in smooth muscle phenotype from a quiescent, contractile state to a migrating, proliferative form; (2) migration of the transformed smooth muscle cell from the media to the intima; and (3) massive proliferation of smooth muscle cells in the intima. Investigations of the pathogenesis of intima thickening have produced a theory that, following arterial injury, platelets, endothelial cells, macrophages and smooth muscle cells release various cytokines such as interleukin-1 (1L-1) and paracrine and autocrine growth factors such as platelet derived growth factor, epidermal growth factor, insulin-like growth factor, and fibroblast growth factor. T-cells and macrophages also migrate into the neointima. This cascade of events, as it has been suggested, results in an excessive proliferation and migration of smooth muscle cells, which causes the narrowing of the blood vessel and the reduction of the flow of blood through the vessel.

No surgical intervention or post-surgical treatment, to date, has proven significantly effective in preventing restenosis. Treatment strategies have included repeat balloon remodeling or implantation of stents. Stents are scaffoldings, usually cylindrical or tubular in shape, which function to physically hold open and, if desired, to expand the wall of the passageway. Typically stents are capable of being compressed, so that they can be inserted through small cavities via catheters, and then expanded to a larger diameter once they are at the desired location. Mechanical intervention via stents, although a significant innovation in the treatment of occlusive regions, has not reduced the development of restenosis.

Pharmaceutical agents have also been locally and systemically administered, concurrent with or following PTI, in an attempt to inhibit smooth muscle cell hyper-proliferation. The pharmaceutical agents employed in an attempt to treat restenosis have shown some favorable result. However, there is a great need for better and more effective compounds, and methods of using the compounds for the effective management of restenosis.

SUMMARY OF THE INVENTION

In accordance with one aspect of the invention, a stent is provided including a radially expandable tubular body for being implanted in a mammalian blood vessel. The stent carries a therapeutic substance such as a podophyllotoxin, cephalotin, trapidil, ticlopidine, tranilast, a IIb-IIIa inhibitor, clobetasol, a Cox-2 inhibitor, PGE1, alprostadil, bleomycin, curcimin, dipyridamole, tirofiban, verapamil, vitronectin, argatroban, carboplatin, or a combination thereof. Representative examples of the podophyllotoxins inlcude etoposide and teniposide. One example of an IIb-IIIa inhibitor is eptifibatide and examples of Cox-2 inhibitors include celecoxib or rofecoxib. Other therapeutic substances can include ENDOSTATIN, ANGIOSTATIN, thalidomide and 2-methoxyestraidol. A polymeric coating supported by the stent can carry the therapeutic substance.

In accordance with another aspect of the present invention a therapeutic method is provided for inhibiting restenosis of a blood vessel by administering to a mammal one of the aforementioned therapeutic substances. The administration can be local, systemic, oral, parenteral, via a catheter, via an implantable device such as a self-expandable stent, balloon-expandable stent, or a graft. The restenosis can be the result of a vascular trauma associated with angioplasty, placement of a stent, or grafting, such that the therapeutic substance can be locally administered to a designated region of the blood vessel subsequent to the vascular trauma.

In accordance with another aspect of the invention, a method for positive remodeling of a blood vessel wall is provided. One of the aforementioned therapeutic substances can be applied to the blood vessel wall such that at least one layer of the blood vessel wall undergoes positive remolding.

DETAIL DESCRIPTION OF THE EMBODIMENTS

Figure 1:
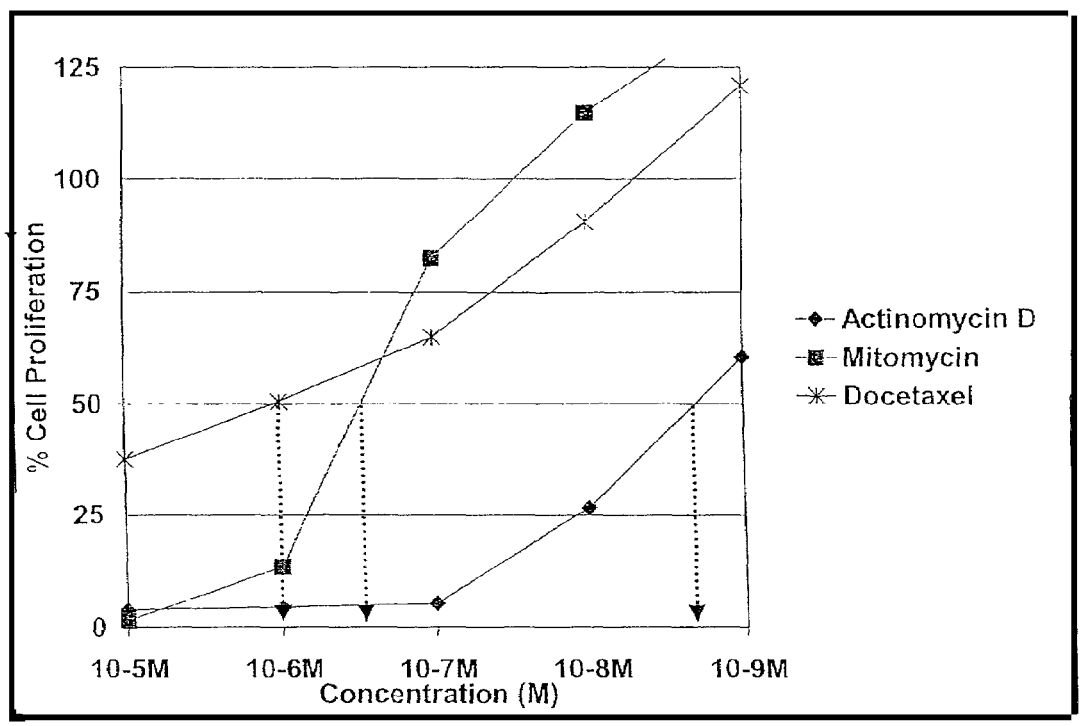
FIG. 1 graphically depicts in vitro experimental data showing affects of actinomycin D, mitomycin and docetaxel on smooth muscle cell proliferation.

Active components and methods of using the active components are provided for inhibiting the activity of vascular smooth muscle cells, abnormal or inappropriate migration and/or proliferation of smooth muscle cells, local inflammatory reaction, angiogenesis, and other activities leading to at least the partial occlusion of a vessel or restenosis. The active components can be for enhancing wound healing in a vascular site, improving the structural and elastic properties of the vascular site, and/or inducing the positive remodeling of the vascular walls.

"Smooth muscle cells" include those cells derived from the medial and adventitia layers of the vessel which proliferate in intimal hyperplastic vascular sites following vascular trauma or injury.

"Migration" of smooth muscle cells means movement of these cells in vivo from the medial layers of a vessel into the intima.

"Proliferation" of smooth muscle cells means increase in cell number.

"Abnormal" or "inappropriate" proliferation means division, growth and/or migration of cells occurring more rapidly or to a significantly greater extent than typically occurs in a normally functioning cell of the same type, i.e., hyper-proliferation.

"Inhibiting cellular activity" means reducing, delaying or eliminating smooth muscle cell hyperplasia, restenosis, and vascular occlusions, particularly following biologically or mechanically mediated vascular injury or trauma or under conditions that would predispose a mammal to suffer such a vascular injury or trauma. As used herein, the term "reducing" means decreasing the intimal thickening that results from stimulation of smooth muscle cell proliferation. "Delaying" means retarding the progression of the hyper-proliferative vascular disease or delaying the time until onset of visible intimal hyperplasia, as observed, for example, by histological or angiographic examination. "Elimination" of restenosis following vascular trauma or injury means completely "reducing" and/or completely "delaying" intimal hyperplasia in a patient to an extent which makes it no longer necessary to surgically intervene, i.e., to re-establish a suitable blood flow through the vessel by, for example, repeat angioplasty, atheroectomy, or coronary artery bypass surgery. The effects of reducing, delaying, or eliminating restenosis may be determined by methods known to one of ordinary skill in the art, including, but not limited to, angiography, ultrasonic evaluation, fluoroscopy imaging, fiber optic visualization, or biopsy and histology. Biologically mediated vascular injury includes, but is not limited to injury caused by or attributed to autoimmune disorders, alloimmune related disorders, infectious disorders including endotoxins and herpes viruses such as cytomegalovirus, metabolic disorders such as atherosclerosis, and vascular injury resulting from hypothermia and irradiation. Mechanical mediated vascular injury includes, but is not limited to vascular injury caused by catheterization procedures or vascular scraping procedures such as percutaneous transluminal coronary angioplasty, vascular surgery, stent placement, transplantation surgery, laser treatment, and other invasive procedures which disrupted the integrity of the vascular intima or endothelium. The active component of the invention is not restricted in use for therapy following vascular injury or trauma; rather, the usefulness of the component will also be determined by the component's ability to inhibit cellular activity of smooth muscle cells or to inhibit the development of restenosis.

"Inhibiting angiogenesis" means reducing, delaying, or eliminating vascular in-growth in the stenotic region which can promote the development of restenosis. "Reducing," "delaying" or "eliminating" means decreasing, retarding the progression of, or completely "reducing" and/or completely "delaying" the formation of new blood vessels and/or decreasing the size and/or number of previously existing vessels. A variety of methods can be readily utilized to determine the anti-angiogenic activity of a given compound, including for example, chick chorioallantoic membrane ("CAM") assays. Briefly, as is understood by one of ordinary skill in the art, a portion of the shell from a fertilized chick egg is removed, and, for example, a methyl cellulose disk containing a sample of the anti-angiogenic compound to be tested is placed on the membrane. After several days, e.g., 48 hours, inhibition of vascular growth by the sample to be tested may be readily determined by visualization of the CAM in the region surrounding the methyl cellulose disk. Inhibition of vascular growth may also be determined quantitatively, for example, by determining the number and size of blood vessels surrounding the methyl cellulose disk, as compared to a control methyl cellulose disk.

"Other activities" means any factor leading to at least the partial occlusion of a vessel and restenosis including, for example, aggregation of blood factors, primarily platelets, fibrin, or the like, with the entrapment of cellular elements.

"Inflammatory reaction" is generally referred to the local cellular response to mechanically or biologically mediated vascular injury that can be marked by capillary dilation and leukocytic infiltration.

"Restenosis" is defined as at least partial reclosure of previously stenosed and subsequently dilated or remodeled vessel, for example, more than 50% stenosis of the vessel. A strong correlation between restenosis and local inflammatory reaction is observed. Inflammatory reaction can be in response to, for example, vascular injury caused by catheterization procedures or vascular procedures such as PTCA, stent placement, vascular surgery, transplantation surgery, laser treatment, and other invasive procedures which disrupt the integrity of the vascular intima or endothelium. The expression of vascular cell adhesion molecules (VCAM-1) is often upregulated in areas of low hemodynamic flow, such as behind stent struts or downstream from protruding plaques. The upregulation of VCAM-1 expression leads to enhanced binding of inflammatory cells, like monocytes, in the area of low hemodynamic flow. Activated monocytes have been correlated with restenosis following balloon angioplasty. Pietersma et al., "Late Lumen Loss After Coronary Angioplasty is Associated with Activation Status of Circulating Monocytes Before Treatment" Circulation 91, 1320 (1995). The correlation is drawn stronger by studies reported by F. Crea, "Screening For The Restenosis Subgroup: The Role of Humoral Factors" $5^{th}$ Int. Conference On Local Drug Delivery and Radiation, Geneva #15 (1999), in which for clinical studies of humoral markers for inflammation, it was found that the degree of activation of inflammatory cells in patients undergoing PTCA, as measured by circulating levels of C-reactive protein in the blood, was a useful predicator of the development of obstructive restenotic plaque. In studies published by Moreno et al., "Macrophage Infiltration Predicts Restenosis After Coronary Intervention in Patients with Unstable Angina" Circulation 94, 3098 (1996), the composition of coronary atherectomy tissue was investigated in patients undergoing PTCA without stenting. Subsequent to the procedure, the degree of restenosis in the patients was measured at 30 days by quantitative angiography. Restenosis was defined as >50% stenosis of the vessel. The atherectomy tissue recovered from the group that went on to develop restenosis contained about twice the amount of macrophages compared to those in patients that did not develop the disease.

"Positive remodeling" is generally defined as the ability of the vessel walls to structurally adapt, by increasing in lumen size, to chronic stimuli. A positively remodeled lumen wall has a greater diameter or size as compared to a lumen wall which has not been subjected to the remodeling effect. Accordingly, the flow of blood through the remodeled site is increased—flow which would have otherwise been reduced because of, for example, the presence of plaque build-up or migration and proliferation of cells. The index of remodeling is defined by the ratio of the area circumscribed by the external elastic lamia (EEL) of the lesion site to the area circumscribed by the EEL of a reference site. As a result of the positive remodeling of the EEL, the internal elastic lamina (IEL), in response, can also increases in area or diameter.

Representative embodiments of the active component include actinomycin D (available from Sigma-Aldrich; or Cosmegen® available from Merck) or derivatives, analogs or synonyms thereof, such as dactinomycin, actinomycin IV, actinomycin $I_1$, actinomycin $X_1$, and actinomycin $C_1$; podophyllotoxins such as etoposide and teniposide (Bristol Myers Squibb and Sigma Chemical); cephalotin (Bristol Myers Squibb); trapidil; ticlopidine (Danbury Pharma, Genpharm); tranilast (SmithKline Beecham and LG Chemical Kissei, Japan); IIb-IIIa inhibitors such as eptifibatide (COR therapeutic); clobetasol (Glaxo Wellcome); COX-2 inhibitors such as celecoxib (CELEBREX)(Searle and Pfizer) and rofecoxib (VIOXX) (Merck); PGE1 or alprostadil (Bedford); bleomycin; ENDOSTATIN (EntreMed); ANGIOSTATIN (EntreMed); thalidomide; 2-methoxyestraidol (EntreMed and Sigma Chemical); curcimin (the major constituent of turmeric powder extract from the rhizomes of the plant *Curcuma longa L* found in South and Southeast tropical Asia); cisplatin (Sigma Chemical); dipyridamole; tirofiban; verapamil; vitronectin; argatroban; and carboplatin (Sigma Chemical). Additionally, corticosteroids such as anti-inflammatory glucocorticoids including clobetasol, diflucortolone, flucinolone, halcinonide, and halobetasol can also be used. In one embodiment, faster acting non-steroidal anti-inflammatory agents such as naproxen, aspirin, ibuprofen, fenoprofin, idomethacin, and phenylbutazone can be used inconjunction with the glucocorticoids. The use of a non-steroidal anti-inflammatory agent is useful during the early stages of the inflammation in response to a mechanically mediated vascular injury.

The active component can be formulated with a pharmaceutical carrier of solid or liquid form. A solid carrier can include one or more substances which may act as flavoring agents, lubricants, solubilizers, suspending agents, fillers, glidants, compression aids, binders or tablet-disintegrating agents. Additionally, the solid carrier can be an encapsulating material or a polymeric carrier for sustained delivery. In powder, the carrier is a finely divided solid which is in admixture with the finely divided active component. In tablets, the active component is mixed with a carrier having the necessary compression properties in suitable proportions and compacted in the shape and size desired. The powder and tablets can contain up to about 99% of the active component. Suitable solid carrier include, for example, calcium phosphate, magnesium stearate, talc, sugars, lactose, dexyin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active component can be dissolved or suspended in a pharmaceutically acceptable liquid carrier such as water or suitable organic solvents. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carrier for oral and parenteral administration include water, sucrose solution, lipid formulations, phosphate buffered saline solution, alcohols such as monohydric and polyhydric alcohols, and emulsions such as the oil-in-water or water-in-oil type. For parental adminstration, the carrier can also be an oily ester such as ethyl oleate and isopropyl myristate. The liquid carrier for pressurized compositions can be, for example, a halogenated hyrdrocarbon.

The administration of the active component can be accomplished systemically or locally. Systemic administration can be accomplished orally or parenterally including intravascularly, rectally, intranasally, intrabronchially, or transdermally. Liquid carriers which are sterile solutions or suspensions can be injected intramuscularly, intraperitoneally, subcutaneously, and intravenously. Rectal administration can be in the form of conventional suppository. For adminsitration by intranasal or intrabronchial inhalation or insufflation, the active component can be formulated into an aqueous or partially aqueous solution, which can then be utilized in the form of an aerosol. The active component can be administered transdermally through the used of a transdermal patch and a carrier that is inert to and mutually compatible with the active component, is non-toxic to the skin, and allows for the delivery of the active component for systemic absorption into the blood stream via the skin. The carrier may take any number of forms such as creams, ointments, pastes, and gels. The creams and ointments may be viscous liquids or semisolid emulsions of either the oil-in-water or water-in-oil type. Pastes made of absorptive powders dispersed in petroleum or hydrophilic petroleum containing the active component may also be suitable. Other devices capable of releasing the active component into the blood stream include semi-permeable membranes covering a reservoir containing the active component, with or without a carrier.

Local administration can be accomplished by a variety of techniques which administer the active component at or near the target site. The following examples of local delivery techniques are provided for illustrative purposes and are not intended to be limiting. Examples include local delivery catheters, site specific carriers, implants, direct application, or direct injection. Local delivery by a catheter allows for the administration of the active component directly to the proliferative lesion. Local delivery by site specific carriers is conducted by attaching the active component to a carrier which will direct or link the drug to the proliferative cells. Examples of this delivery technique include the use of carrier such as a protein ligand, a monoclonal antibody or a membrane anchored linker.

Local delivery by an implant is the placement of a matrix carrying the active component at the proliferative site. The matrix can release the active component by, for example, diffusion, degradation, chemical reaction, solvent activators, etc. One example of local delivery by an implant can include direct injection of vesicles or micro-particles into the proliferative site. These micro-particles may be composed of substances such as proteins, lipids, carbohydrates or synthetic polymers. The micro-particles can have the active component impregnated therein and/or coated thereon.

Yet in another example, a delivery system is provided in which a polymer that contains the active component is injected into the lesion in liquid form. The polymer can then be cured to form the implant in situ. In situ polymerization can be accomplished by photocuring or chemical reaction. Photocuring is conducted by mixing a polymer such as, but not limited to, acrylate or diacrylate modified polyethylene glycol (PEG), pluronic, polybutylene teraphthalate-co-polyethylene oxide, polyvinyl alcohol, hydroxy ethyl methacrylate (HEMA), hydroxy ethyl methacrylate-co-polyvinyl pyrrolidone, HEMA-co-PEG, or glycidol acrylate modified Heparin or sulfated dextran with the active component, with or without a photosensitizer (e.g., benzophenone) or a photoinitiator (e.g., 2,2 dimethoxy 2-phenyl acetophenone, and eosin-Y). The precursor system can be activated by a suitable wavelength of light corresponding to the system. The activation will result in a cured system that incorporates the active component.

Chemical reaction can be conducted by incorporating di-isocyanate, aldehyde, N-hydroxy-succinimide, di-imidazole, —NH2,—COOH, with a polymer such as PEG or HEMA. The process of photocuring and chemical reaction is known to one of ordinary skill in the art.

Application via implants is not limited to the above described routes and other techniques such as grafts, micro-pumps or application of a fibrin glue or hydrogel containing the active component around the exterior of a designated region of the adventitia can also be implemented by one of ordinary skill in the art.

Local delivery by direct application includes the use of topical applications. An example of a local delivery by direct application is applying the active component directly to the arterial bypass graft during the surgical procedure. Another example of local delivery by direct application includes delivery of the active component into the pericardial sac as is known by one of ordinary skill in the art.

Local delivery by direct injection describes injecting a liquid carrier containing the active component directly into the proliferative site. The liquid carrier should be inert to and mutually compatible with the active component. The component can be in true solution or suspended in fine particles in the carrier. A suitable example of an inert carrier includes a sterile saline solution.

As another example, the active component can be administered in a single, sustained delivery treatment via a stent, such as a balloon-expandable or self-expandable stent. The stent can include cavities, micro-depots or holes, reservoirs or a coating, such as a polymeric film layer, which can contain and release the active component by diffusion, degradation, desolution, chemical reaction, etc. The micro-depots or holes can be etched or created by a laser discharge. The polymeric coating can be any suitable polymeric compound that is mutually compatible with the active component. Suitable examples of polymeric compounds for the coating include, but are not limited to, polycaprolactone (PCL), poly-D,L-lactic acid (DL-PLA), poly-L-lactic acid (L-PLA), poly(lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates, fibrin, fibrinogen, cellulose, starch, collagen, parylene, PARYLAST (available from Advanced Surface Technology Product), polyurethane, polyethylene, polyethylene teraphthalate, ethylene vinyl acetate, silicone, polyethylene oxide, ethylene vinyl alcohol copolymer (commonly known by the generic name EVOH or by the trade name EVAL), and mixtures thereof.

EVOH possesses qualities that are desirable in stent coatings. Such qualities include, but are not limited to, susceptibility to expansion with the sent without any significant detachment from the surface of the stent; allowance for significant control of the release rate of the active component; and strong adherence to the surface of the stent, specially metallic material such as stainless steel. The self-expandable stent can be coated by any conventional method, such as by spraying the polymeric solution onto the surface of the stent or immersing the stent in the composition. By way of example, EVOH can be added to a dimethylsufoxide (DMSO), dimethyl acetamide (DMAC), or an iso-propylalcohol (IPA)/$H_2O$ (for EVOH having 27 to 29 mol % ethylene content) solvent followed by the addition of the active component to the blend. IPA can include, for example, form about 40% to about 60% by weight of the total weight of the solvent.

In this embodiment, the EVOH can include from about 0.1% to about 35%, more narrowly from about 12% to about 20% by weight of the total weight of the solution; the solvent can include from about 59.9% to about 99.8%, more narrowly from about 79% to about 87% by weight of the total weight of the solution; and the active component can include from about 0.1% to about 40%, more narrowly from about 1% to about 9% by weight of the total weight of the solution. In accordance with another embodiment the active component can be blended in a solution of EVOH, DMSO, and a wetting fluid. The inclusion of the wetting fluid results in the application of a more uniform coating. The suitable wetting fluid typically has a high capillary permeation and should have a viscosity not greater than bout 50 centipoise, usefully about 0.3 to about 5 centipoise, more narrowly about 0.4 to about 2.5 centipoise in ambient temperature. The wetting fluid should be mutually compatible with the other ingredients used in the formulation and should not precipitate the copolymer. Useful examples of the wetting fluid include, but are not limited to, tetrahydrofuran (THF), dimethylformamide (DMF), 1-butanol, and mixtures and combinations thereof. In this embodiment, the ethylene vinyl alcohol copolymer can include from about 0.1% to about 35%, more narrowly from about 10% to about 25% by weight of the total weight of the solution; the solvent can include from about 19.8% to about 98.8%, more narrowly from about 49% to about 79% by weight of the total weight of the solution; the wetting fluid can include from about 1% to about 80%, more narrowly from about 5% to about 40% by weight of the total weight of the solution; and the active component can include from about 0.1% to about 40%, more narrowly from about 1% to about 9% by weight of the total weight of the solution.

Systemic or local administration via the various disclosed routes may be continuous, intermittent, applied in a single treatment or multiple treatments. For example a regiment can be contemplated which involves a single dose given before and/or at the time of the treatment procedure, e.g., PCTA, and with a follow-up dose delivered after a predetermined time period subsequent to the treatment procedure. The dosage or concentration of the active component required to produce a favorable therapeutic effect should be less than the level at which the active component produces toxic effects and greater than the level at which non-therapeutic results are obtained. The dosage or concentration of the active component required to inhibit the desired cellular activity of the vascular region can depend upon factors such as the particular circumstances of the patient; the nature of the trauma; the nature of the therapy desired; the method of administration e.g., the binding affinity of the vascular smooth muscle cell binding protein; the time over which the active component administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

The invention will be better understood by making reference to the following examples which are being provided by way of illustration and are not intended to unduly limit the scope of the present invention. The effect of actinomycin D to control cellular proliferation and intimal thickening is demonstrated by in vitro and in vivo studies.

EXAMPLE 1

Inhibition of SMC Proliferation with Actinomycin D

Medial smooth muscle cells (SMC) were isolated from rat aorta and cultured according to explant methods known to one of ordinary skill in the art. Cells were harvested via trypsinization and subcultivated. Cells were identified as vascular SMC through their characteristic hill-and-valley growth pattern as well as indirect immunofluorescence with monoclonal anti SMC α-actin. Studies were performed with cells at passage 3-4. SMC monlayers were established on 24 well culture dishes, scrape wounded and treated with actinomycin D, mytomycin and docetaxel. The cells were exposed to the drug solution of different concentrations for 2 hours and then washed with buffered saline solution. The proliferation of the cells was quantified by standard technique of thymidine incorporation. The results from the study are tabulated in FIG. 1.

The $IC_{50}$ (concentration at which 50% of the cells stop proliferating) of actinomycin D was $10^{-9}$M as compared to $5 \times 10^{-5}$M for mitomycin and $10^{-6}$M for docetaxel. Actinomycin D was the most potent agent to prevent SMC proliferation as compared to other pharmaceutical agents.

EXAMPLE 2

Reduction in Restenosis in the Porcine Coronary Artery Model

Porcine coronary models were used to assess the degree of the inhibition of neointimal formation in the coronary arteries of a porcine stent injury model by Actinomycin D, delivered with a microporous balloon catheter ($1 \times 10^6$ pores/cm$^2$ with size ranging from 0.2-0.8 micron).

The preclinical animal testing was performed in accordance with the NIH Guide for Care and Use of Laboratory Animals. Domestic swine were utilized to evaluate effect of the drug on the inhibition of the neointimal formation. Each testing procedure, excluding the angiographic analysis at the follow-up endpoints, was conducted using sterile techniques. During the study procedure, the activated clotting time (ACT) was monitored regularly to ensure appropriate anticoagulation. Base line blood samples were collected for each animal before initiation of the procedure. Quantitative coronary angiographic analysis (QCA) and intravascular ultrasound (IVUS) analysis was used for vessel size assessment.

The vessels at the sites of the delivery were denuded by inflation of the PTCA balloons to 1:1 balloon to artery ratio and moving the balloons back and forth 5 times. Actinomycin D was delivered to the denuded sites at 3.5 atm (3.61 kg/sq. cm) for 2 minutes using the microporous balloon catheters before stent deployment. The average volume of delivery was about 3.3+/−1.2 ml. Following drug delivery, stents were deployed at the delivery site such that final stent to artery ratio was 1.1:1.

QCA and IVUS analyses were used for stent deployment guidance. Pre-stenting IVUS measurements of the lumen size at the targeted vessel sites were performed for determination of the balloon (size) inflation pressure. Quantitative analysis of the stented coronary arteries to compare pre-stenting, post-stenting, follow-up minimal luminal diameters, stent recoil, and balloon/stent to artery ratio were performed. Following stent implantation and final angiogram, all devices were withdrawn and the wounds closed; the animals were allowed to recover from anesthesia as managed by the attending veterinarian or animal care professionals at the research center.

Upon return to the research laboratory at the 28-day endpoint, angiographic assessments were performed. Coronary artery blood flow was assessed and the stented vessels were evaluated to determine minimal lumen diameter. The animals were euthanized following this procedure at the endpoint. Following euthanasia, the hearts were pressure perfusion fixed with formalin and prepared for histological analysis, encompassing light microscopy, and morphometry. Morphometric analysis of the stented arteries included assessment of the position of the stent struts and determination of vessel/lumen areas, percent (%) stenosis, injury scores, intimal and medial areas and intima/media ratios. Percent stenosis is quantitated by the following equation:

$$100(\text{IEL area} - \text{lumen area})/\text{IEL area}$$

where IEL is the internal elastic lamia.

Figure 2A:
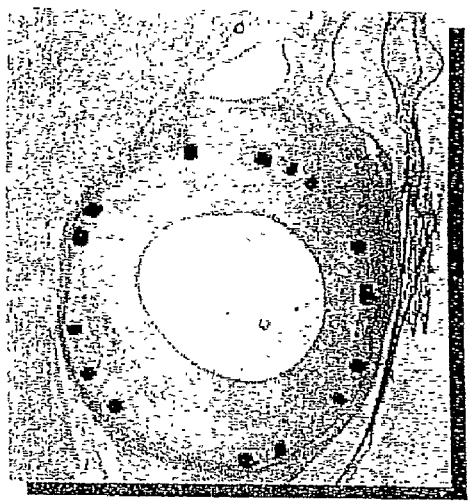
FIG. 2A is a picture of a histology slide of a coronary vessel from the control group in accordance with Example 2.
Figure 2B:
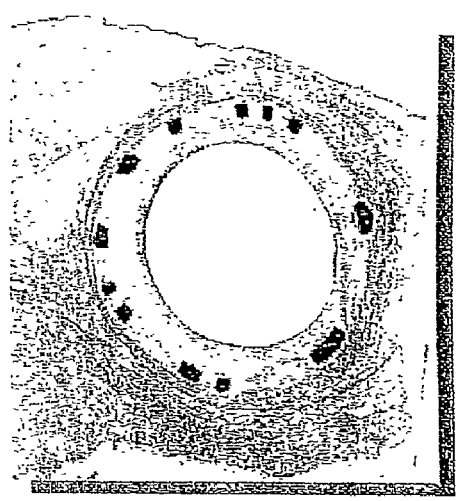
FIG. 2B is a picture of a histology slide of a coronary vessel from the actinomycin D group in accordance with Example 2.

The control group of animals received delivery of water instead of the drug. The test group of animals received actinomycin D in two different concentration of $10^{-5}$M and $10^{-4}$M. The results of the study are tabulated in Table 1. The percent stenosis in the treated groups (32.3+/−11.7) was significantly decreased as compared to the control groups (48.8+/−9.8). FIGS. 2A and 2B illustrate sample pictures of the histology slides of the coronary vessels from the control and the Dose 1 group, respectively.

TABLE 1

|  | CONTROL 0 M | DOSE 1 1E−05 M | DOSE 2 1E−04 M | t test (significant if p < 0.05) | |
|---|---|---|---|---|---|
|  | (n = 9) | (n = 10) | (n = 7) | p~ | p* |
| ANGIOGRAPHIC DATA (QCA) | | | | | |
| Percent Diameter Stenosis | 48.8 +/− 9.8 | 36.8 +/− 9.7 | 32.3 +/− 11.7 | 0.02 | 0.01 |
|  | CONTROL 0 M | DOSE 1 1E−05 M | DOSE 2 1E−04 M | t test (significant if p < 0.05) | |
|  | (n = 27) | (n = 30) | (n = 21) | p~ | p* |

TABLE 1-continued

HISTOMORPHOMETRIC DATA

| | | | | | |
|---|---|---|---|---|---|
| Percent Stenosis (IEL area-lumen area)/IEL area | 63.4 +/− 12.7 | 51.8 +/− 13.8 | 54.1 +/− 11.7 | 0.002 | 0.01 |
| Residual Lumen (Lumen area)/IEL area | 0.36 +/− 0.16 | 0.49 +/− 0.14 | 0.46 +/− 0.08 | 0.002 | 0.01 |

~comparison between control and Dose 1
*comparison between control and Dose 2

The results of the in vitro and in vivo standard test procedures demonstrate that actinomycin D is useful for the treatment of hyper-proliferative vascular disease. Specifically, actinomycin D is useful for the inhibition of smooth muscle cell hyperplasia, restenosis and vascular occlusion in a mammal, particularly occlusions following a mechanically mediated vascular trauma or injury.

EXAMPLE 3

In vivo data is provided illustrated positive remodeling caused by the application of actinomycin D. Stents coated with EVAL impregnated with actinomycin D and a control group of stents coated with EVAL free from actinomycin D were implanted in porcine coronary arteries. The animals were sacrificed at the end of 28 days. The EEL area of the actinomycin D-loaded vessels was statistically significantly greater than the EEL area of the control vessels. The index of remodeling was 1.076 (8.54/7.94).

| Condition | Mean Area | Std Dev |
|---|---|---|
| IEL | | |
| Drug coated (Act-D in EVAL) | 7.47 | 0.89 |
| Control (EVAL) | 6.6 | 0.61 |
| p value | 0.0002 | Statistical significant difference |
| EEL (external elastic lamia) | | |
| Drug coated (Act-D in EVAL) | 8.54 | 0.87 |
| Control (EVAL) | 7.94 | 0.73 |
| p value | 0.014 | Statistical significant difference |

EEL Area (mm$^2$)

| ID # | Control | ID # | Actinomycin D | ID # | EVAL |
|---|---|---|---|---|---|
| 48 LCX d | 6.3966 | 63 LCX d | 7.4498 | 63 LAD d | 8.3037 |
| 48 LCX m | 7.4601 | 63 LCX m | 8.2509 | 63 LAD m | 8.8545 |
| 48 LCX p | 7.3063 | 63 LCX p | 7.7342 | 63 LAD p | 9.4698 |
| 49 LAD d | 8.5573 | 63 RCA d | 7.9207 | 64 LCX d | 7.8063 |
| 49 LAD m | 8.5187 | 63 RCA m | 6.9926 | 64 LCX m | 7.1117 |
| 49 LAD p | 6.6346 | 63 RCA p | 8.3883 | 64 LCX p | 7.2411 |
| 58 LAD d | 8.6078 | 65 LAD d | 7.8546 | 64 RCA d | 8.3383 |
| 58 LAD m | 8.1674 | 65 LAD m | 9.2545 | 64 RCA m | 8.0793 |
| 58 LAD p | 8.3775 | 65 LAD p | 9.2515 | 64 RCA p | 8.3652 |
| 59 LCA d | 8.3054 | 68 LAD d | 8.7854 | 65 LCX d | 6.4638 |
| 59 LCX m | 7.3713 | 68 LAD m | 9.5164 | 65 LCX m | 7.1493 |
| 59 LCX p | 7.8662 | 68 LAD p | 9.1504 | 65 RCA d | 8.5955 |
| 59 RCA d | 7.3714 | 69 LCX d | 9.6679 | 65 RCA m | 8.0855 |
| 59 RCA m | 6.6783 | 69 LCX m | 9.1237 | 65 RCA p | 8.4785 |
| 59 RCA p | 7.4707 | 69 LCX p | 9.9849 | 68 LCX d | 8.4723 |
| 62 LCX d | 7.8784 | 69 RCA d | 9.4765 | 68 LCX m | 7.8382 |
| 62 LCX m | 7.5318 | 69 RCA m | 7.4424 | 68 LCX p | 8.0570 |
| 62 LCX p | 6.2647 | 69 RCA p | 9.1462 | 68 RCA d | 8.4840 |
| 62 RCA d | 8.3240 | 70 LCX d | 8.9504 | 68 RCA p | 8.8767 |
| 62 RCA m | 7.9535 | 70 LCX m | 8.9117 | 69 LAD d | 6.6648 |
| 62 RCA p | 8.5454 | 70 LCX p | 8.7533 | 69 LAD m | 6.8614 |
| 67 LAD d | 8.9532 | 70 RCA d | 7.3249 | 69 LAD p | 7.7632 |
| 67 LAD m | 9.2410 | 70 RCA m | 7.1061 | 70 LAD d | 7.5175 |
| 67 LAD p | 8.3841 | 70 RCA p | 8.5830 | 70 LAD m | 7.8630 |
| | | | | 70 LAD p | 8.2222 |
| AVG | 7.8402 | | 8.5425 | | 7.9475 |
| SD | 0.8046 | | 0.8755 | | 0.7349 |

ActD vs EVAL

| | |
|---|---|
| p = | 0.014709 |
| AVG % EEL growth | 7.486304 |

IEL Area (mm2)

| ID # | Control | ID # | Actinomycin D | ID # | EVAL |
|---|---|---|---|---|---|
| 48 LCX d | 5.2178 | 63 LCX d | 6.3785 | 63 LAD d | 6.9687 |
| 48 LCX m | 6.2108 | 63 LCX m | 7.5206 | 63 LAD m | 7.3908 |
| 48 LCX p | 6.1125 | 63 LCX p | 6.9992 | 63 LAD p | 7.3563 |
| 49 LAD d | 7.2848 | 63 RCA d | 6.9632 | 64 LCX d | 6.4420 |
| 49 LAD m | 7.4117 | 63 RCA m | 6.0418 | 64 LCX m | 6.0064 |
| 49 LAD p | 5.9918 | 63 RCA p | 7.4794 | 64 LCX p | 5.9970 |
| 58 LAD d | 7.2049 | 65 LAD d | 6.2324 | 64 RCA d | 6.8001 |
| 58 LAD m | 6.9334 | 65 LAD m | 8.3785 | 64 RCA m | 6.8561 |
| 58 LAD p | 6.9454 | 65 LAD p | 8.5819 | 64 RCA p | 7.0172 |
| 59 LCA d | 7.2640 | 68 LAD d | 8.0964 | 65 LCX d | 5.2485 |
| 59 LCX m | 6.2014 | 68 LAD m | 8.6879 | 65 LCX m | 6.1135 |
| 59 LCX p | 6.7283 | 68 LAD p | 8.0914 | 65 RCA d | 7.1525 |
| 59 RCA d | 6.0519 | 69 LCX d | 8.7181 | 65 RCA m | 6.4815 |
| 59 RCA m | 5.9992 | 69 LCX m | 8.0273 | 65 RCA p | 7.1775 |
| 59 RCA p | 5.9032 | 69 LCX p | 8.5222 | 68 LCX d | 6.9571 |
| 62 LCX d | 6.5329 | 69 RCA d | 8.3796 | 68 LCX m | 6.5724 |
| 62 LCX m | 6.2804 | 69 RCA m | 6.4219 | 68 LCX p | 6.7740 |
| 62 LCX p | 4.9303 | 69 RCA p | 7.7757 | 68 RCA d | 7.2425 |
| 62 RCA d | 7.0977 | 70 LCX d | 7.5392 | 68 RCA p | 7.5554 |
| 62 RCA m | 6.7466 | 70 LCX m | 7.6573 | 69 LAD d | 5.5505 |
| 62 RCA p | 7.1747 | 70 LCX p | 6.9749 | 69 LAD m | 5.5571 |
| 67 LAD d | 8.0264 | 70 RCA d | 6.2815 | 69 LAD p | 6.2697 |
| 67 LAD m | 8.1144 | 70 RCA m | 5.9760 | 70 LAD d | 6.3212 |
| 67 LAD p | 7.2091 | 70 RCA p | 7.6195 | 70 LAD m | 6.6518 |
| | | | | 70 LAD p | 6.9032 |
| AVG | 6.6489 | | 7.4727 | | 6.6025 |
| SD | 0.7883 | | 0.8972 | | 0.6130 |

ActD vs EVAL

| | |
|---|---|
| p = | 0.000283 |
| AVG % IEL growth | 13.17981 |

Figure 3A:
FIG. 3A is a picture of a histology slide of a coronary vessel from the control group in accordance with Example 3.
Figure 3B:
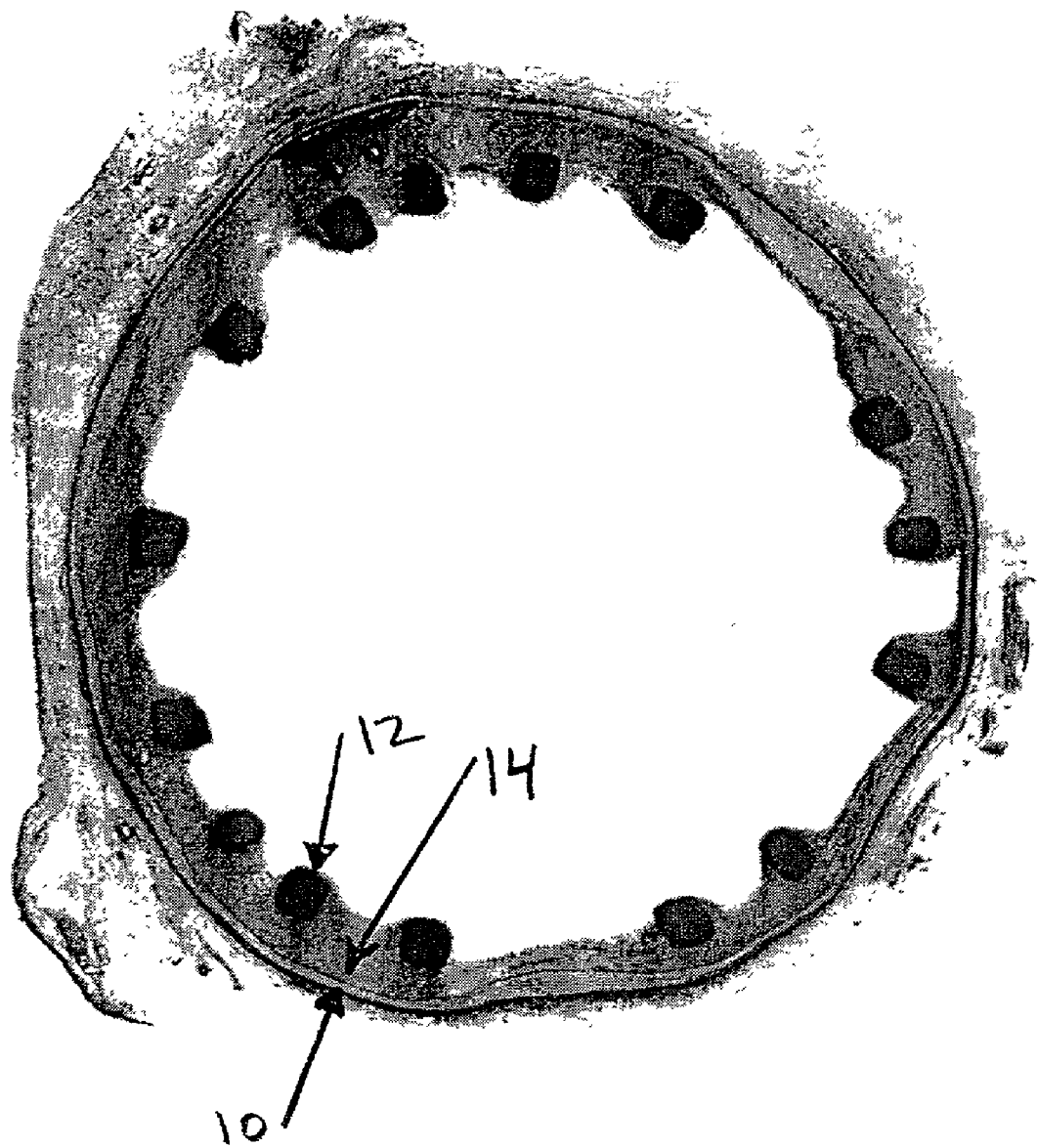
FIG. 3B is a picture of a histology slide of a coronary vessel from the actinomycin D group in accordance with Example 3.

FIGS. 3A and 3B illustrate sample pictures of the histology slides of the coronary vessels from the control group 64 RCA (Right Coronary Group) and the actinomycin D loaded stent group 68 LAD (Left Anterior Descending), respectively. The stent used was an Advanced Cardiovascular Systems Multi-Link Duet™ (stainless steel). As is illustrated by FIG. 3B, the positive remodeling of IEL 10, caused by the application of actinomycin D, creates a gap between stent struts 12 and IEL 10. Thrombus deposites, illustrated by reference number 14, are formed in the gap over time. The use of a self-expandable stent eliminates the formation of the gap as the stent self-expands in response to the positive remodeling of IEL. Thrombus deposits can be, accordingly, eliminated.

Actinomycin D induces the positive remodeling of the vessel walls, more particularly positive remodeling of the external elastic lamina (EEL) of a blood vessel wall. Positive remodeling is generally defined as the ability of the vessel walls to structurally adapt, by increasing in lumen size, to chronic stimuli. A positively remodeled lumen wall has a greater diameter or size as compared to a lumen wall which has not been subjected to the remodeling effect. Accordingly, the flow of blood through the remodeled site is increased—flow which would have otherwise been reduced because of, for example, the presence of plaque build-up or migration and proliferation of cells. The index of remodeling is defined by the ratio of the area circumscribed by the EEL of the lesion site to the area circumscribed by the EEL of a reference site. As a result of the positive remodeling of the EEL, the internal elastic lamina (IEL), in response, can also increases in area or diameter. Actinomycin D, or analogs or derivative thereof, not only can inhibit abnormal or inappropriate migration and/or proliferation of smooth muscle cells, which can lead to restenosis, but can also induce positive remodeling of the blood vessel walls. Thus the widening of the diseased region becomes more pronounced.

EXAMPLE 4

Multi-Link Duet™ stents (available from Guidant corporation) are cleaned in an ultrasonic bath of isopropyl alcohol for 20 minutes, then air dried. An EVOH stock solution is made having an EVOH:DMSO ratio of 1:4. The mixture is placed in a warm water shaker bath at 60° C. for 12 hours. The solution is mixed, then cooled to room temperature. A 9% by weight actinomycin D solution is formulated as follows: 2.96 grams of the EVOH: DMSO solution is mixed with 0.29 grams of actinomycin D, then 0.9 grams of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. From about 0.05 to about 100 microgram/mm² of actinomycin D can be carried by the stent. More specifically, ranges from about 0.5 to about 20 microgram/mm² and from about 2.5 to about 15 microgram/mm² can also be suitable.

EXAMPLE 5

Multi-Link Duet™ stents (13 mm in length) were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 5.06% by weight actinomycin D solution was formulated as follows: 40 milligrams of actinomycin D was dissolved in 150 milligrams of THF, then 600 milligrams of the EVOH:DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 260 micrograms and an average actinomycin D loading of about 64 micrograms was achieved. The coating was transparent, giving the stents a glossy-like shine.

EXAMPLE 6

Multi-Link Duet™ stents (13 mm in length) were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 3.75% by weight actinomycin D solution was formulated as follows: 60 milligrams of actinomycin D was dissolved in 310 milligrams of DMF, then 1.22 grams of EVOH: DMSO solution was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 270 micrograms with an average actinomycin D content of about 51 micrograms was achieved. The coating was transparent, giving the stents a glossy-like shine.

EXAMPLE 7

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 6.1% by weight actinomycin D solution was formulated as follows: 100 milligrams of actinomycin D was dissolved in 310 milligrams of DMF, then 1.22 grams of EVOH:DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 250 micrograms and an average actinomycin D loading of about 75 micrograms was achieved.

EXAMPLE 8

Multi-Link Duet™ stents are cleaned in an ultrasonic bath of isopropyl alcohol for 20 minutes, then air dried. An EVOH stock solution is made having an EVOH:DMSO ratio of 1:40. The mixture is placed in a warm water shaker bath at 60° C. for 12 hours. The solution is mixed, then cooled to room temperature. A 0.60% by weight actinomycin D solution can be formulated as follows: 4920 milligrams of the EVOH: DMSO solution is mixed with 40 milligrams of actinomycin D, then 2000 milligrams of THF is added. The cleaned Multi-Link Duet™ stents can be sprayed upon by the above formulation. The coated stents are cured in a forced air convection oven 60° C. for 15 minutes. Additional layers of the coating are applied and cured in the above manner. The final curing step for the coated stents is conducted for about 4 hours.

While the particular embodiments of the present invention have been shown and described, it will be obvious to those skilled in the art that changes and modifications can be made without departing from this invention in its broader aspect and, therefore, the appended claims are to encompass within their scope all such changes and modifications as fall within the true spirit and scope of this invention.

What is claimed is:

1. A stent, comprising a radially expandable tubular body for being implanted in a mammalian blood vessel, a first therapeutic substance carried by the stent for inhibiting restenosis of the blood vessel, wherein the first therapeutic substance is selected from the group consisting of an anti-inflammatory glucocorticoid, prostaglandin $E_1$, an analog or derivative thereof, tirofiban, an analog or derivative thereof, vitronectin, an analog or derivative thereof, and combinations of any thereof, and a second therapeutic substance selected from the group consisting of naproxen, aspirin, ibuprofen, fenoprofen, idomethacin, and phenylbutazone, and combinations of any thereof and wherein each of the first therapeutic substance and the second therapeutic substance is present at a level that is less than that which produces toxic effects and greater than that at which non-therapeutic results are obtained.

2. The stent of claim 1, wherein the first and second therapeutic substances are carried by a polymeric coating supported by the stent.

3. The stent of claim 2, wherein the polymeric coating comprises an ethylene vinyl alcohol copolymer.

4. The stent of claim 1, wherein the first therapeutic substance is prostaglandin $E_1$.

5. The stent of claim 1, wherein the first therapeutic substance is tirofiban.

6. The stent of claim 1, wherein the first therapeutic substance is vitronectin.

7. The stent of claim 1, wherein the first therapeutic substance is an anti-inflammatory giucocorticoid.

8. The stent of claim 7, wherein the anti-inflammatory glucocorticoid is clobetasol.

* * * * *